United States Patent
Shabaz et al.

(10) Patent No.: US 10,335,127 B2
(45) Date of Patent: Jul. 2, 2019

(54) BIOPSY DEVICE WITH SELECTABLE TISSUE RECEIVING APERATURE ORIENTATION AND SITE ILLUMINATION

(71) Applicant: SenoRx, Inc., Tempe, AZ (US)

(72) Inventors: Martin V. Shabaz, Lake Forest, CA (US); Richard L. Quick, Mission Viejo, CA (US); Frank R. Louw, Carlsbad, CA (US); Paul Lubock, Monarch Beach, CA (US); Jason H. Safabash, Alison Viejo, CA (US)

(73) Assignee: SenoRx, Inc., Franklin Lakes, NJ (US)

( * ) Notice: Subject to any disclaimer, the term of this patent is extended or adjusted under 35 U.S.C. 154(b) by 601 days.

(21) Appl. No.: 14/700,574

(22) Filed: Apr. 30, 2015

(65) Prior Publication Data

US 2015/0230778 A1 Aug. 20, 2015

Related U.S. Application Data

(60) Continuation of application No. 12/229,545, filed on Aug. 25, 2008, now Pat. No. 9,044,215, which is a
(Continued)

(51) Int. Cl.
*A61M 1/00* (2006.01)
*A61B 10/02* (2006.01)
(Continued)

(52) U.S. Cl.
CPC ...... *A61B 10/0266* (2013.01); *A61B 10/0233* (2013.01); *A61B 10/0275* (2013.01);
(Continued)

(58) Field of Classification Search
None
See application file for complete search history.

(56) References Cited

U.S. PATENT DOCUMENTS 2,032,860 A 3/1936 Wappler et al.
3,326,785 A 6/1967 Williams
(Continued)

FOREIGN PATENT DOCUMENTS

CA 2479349 A1 9/2003
CH 602084 A5 7/1978
(Continued)

OTHER PUBLICATIONS

"Adjacent", www.merriam-webster.com/dictionary/adjacent, printed on Apr. 29, 2016, 4 pages.*
(Continued)

*Primary Examiner* — Matthew Kremer

(57) ABSTRACT

A method for collecting a tissue specimen from a target site within a patient includes rotating an elongated tubular section about a longitudinal axis to provide a desired aperture orientation of a tissue receiving aperture; applying a vacuum within the elongated tubular section to draw tissue at the tissue site through the tissue receiving aperture of the elongated tubular section into the interior thereof; advancing an elongated tissue cutting member longitudinally within the elongated tubular section to cut a tissue specimen from the tissue extending into the elongated tubular section; and applying a vacuum to the proximal end of the elongated tissue cutting member for transporting a cut tissue specimen through the inner lumen of the elongated tissue cutting member to discharge the cut tissue specimen directly from the proximal end of the elongated tissue cutting member into a tissue collection device.

11 Claims, 11 Drawing Sheets

Related U.S. Application Data division of application No. 10/911,106, filed on Aug. 3, 2004, now Pat. No. 8,282,573, which is a continuation-in-part of application No. 10/642,406, filed on Aug. 15, 2003, now Pat. No. 7,819,819, which is a continuation-in-part of application No. 10/374,915, filed on Feb. 24, 2003, now Pat. No. 7,189,206.

(51) Int. Cl.

| | | |
|---|---|---|
| A61B 17/00 | (2006.01) | |
| A61B 17/32 | (2006.01) | |
| A61B 17/34 | (2006.01) | |
| A61B 90/00 | (2016.01) | |
| A61B 90/30 | (2016.01) | |
| B23Q 17/24 | (2006.01) | |
| F21V 33/00 | (2006.01) | |

(52) U.S. Cl.
CPC ....... *A61B 10/0283* (2013.01); *A61M 1/0058* (2013.01); *A61B 10/02* (2013.01); *A61B 17/32002* (2013.01); *A61B 17/3417* (2013.01); *A61B 90/30* (2016.02); *A61B 90/39* (2016.02); *A61B 2010/0208* (2013.01); *A61B 2010/0225* (2013.01); *A61B 2017/0046* (2013.01); *A61B 2017/00473* (2013.01); *A61B 2017/3405* (2013.01); *A61B 2017/3454* (2013.01); *A61B 2090/0811* (2016.02); *A61B 2090/309* (2016.02); *B23Q 17/2404* (2013.01); *F21V 33/0068* (2013.01)

(56) References Cited

U.S. PATENT DOCUMENTS

| | | |
|---|---|---|
| 3,805,791 A | 4/1974 | Seuberth et al. |
| 3,844,272 A | 10/1974 | Banko |
| 3,847,153 A | 11/1974 | Weissman |
| 3,902,498 A | 9/1975 | Niederer |
| 3,910,279 A | 10/1975 | Okada et al. |
| 3,945,375 A | 3/1976 | Banko |
| 3,955,578 A | 5/1976 | Chamness et al. |
| 4,007,732 A | 2/1977 | Kvavle et al. |
| 4,202,338 A | 5/1980 | Bitrolf |
| 4,243,048 A | 1/1981 | Griffin |
| 4,294,254 A | 10/1981 | Chamness |
| 4,311,143 A | 1/1982 | Komiya |
| 4,362,160 A | 12/1982 | Hiltebrandt |
| 4,461,305 A | 7/1984 | Cibley |
| 4,503,855 A | 3/1985 | Maslanka |
| 4,565,200 A | 1/1986 | Cosman |
| 4,576,162 A | 3/1986 | McCorkle |
| 4,603,694 A | 8/1986 | Wheeler |
| 4,638,802 A | 1/1987 | Okada |
| 4,643,187 A | 2/1987 | Okada |
| 4,660,267 A | 4/1987 | Wheeler |
| 4,682,606 A | 7/1987 | DeCaprio |
| 4,718,419 A | 1/1988 | Okada |
| 4,724,836 A | 2/1988 | Okada |
| 4,800,896 A | 1/1989 | Jalowayski |
| 4,895,146 A | 1/1990 | Draenert |
| 4,926,858 A | 5/1990 | Gifford, III et al. |
| 4,983,179 A | 1/1991 | Sjostrom |
| 5,007,908 A | 4/1991 | Rydell |
| 5,041,124 A | 8/1991 | Kensey |
| 5,047,027 A | 9/1991 | Rydell |
| 5,059,204 A | 10/1991 | Lawson et al. |
| 5,064,424 A | 11/1991 | Bitrolf |
| 5,080,660 A | 1/1992 | Buelna |
| 5,085,659 A | 2/1992 | Rydell |
| RE33,925 E | 5/1992 | Bales et al. |
| 5,133,359 A | 7/1992 | Kedem |
| 5,133,360 A | 7/1992 | Spears |
| RE34,056 E | 9/1992 | Lindgren et al. |
| 5,158,561 A | 10/1992 | Rydell et al. |
| 5,217,458 A | 6/1993 | Parins |
| 5,219,350 A | 6/1993 | Emerson et al. |
| 5,285,795 A | 2/1994 | Ryan et al. |
| 5,290,303 A * | 3/1994 | Pingleton ......... A61B 17/32002 606/170 |
| 5,311,859 A | 5/1994 | Monroe et al. |
| 5,320,613 A | 6/1994 | Houge et al. |
| 5,324,288 A | 6/1994 | Billings et al. |
| 5,335,671 A | 8/1994 | Clement |
| 5,344,420 A | 9/1994 | Hilal et al. |
| 5,366,468 A | 11/1994 | Fucci et al. |
| 5,374,188 A | 12/1994 | Frank et al. |
| 5,380,321 A | 1/1995 | Yoon |
| 5,395,312 A | 3/1995 | Desai |
| 5,415,656 A | 5/1995 | Tihon et al. |
| 5,417,687 A | 5/1995 | Nardella et al. |
| 5,423,330 A | 6/1995 | Lee |
| 5,423,809 A | 6/1995 | Klicek |
| 5,437,665 A | 8/1995 | Munro |
| 5,441,498 A | 8/1995 | Perkins |
| 5,441,503 A | 8/1995 | Considine et al. |
| 5,470,308 A | 11/1995 | Edwards et al. |
| 5,476,102 A | 12/1995 | Como et al. |
| 5,477,862 A | 12/1995 | Haaga |
| 5,488,958 A | 2/1996 | Topel et al. |
| 5,501,654 A | 3/1996 | Failla et al. |
| 5,507,743 A | 4/1996 | Edwards et al. |
| 5,507,764 A | 4/1996 | Muller |
| 5,526,822 A * | 6/1996 | Burbank ............ A61B 10/0266 600/567 |
| 5,527,331 A | 6/1996 | Kresch et al. |
| 5,538,010 A | 7/1996 | Darr et al. |
| 5,575,794 A | 11/1996 | Walus et al. |
| 5,578,030 A | 11/1996 | Levin |
| 5,595,185 A | 1/1997 | Erlich |
| 5,599,347 A | 2/1997 | Hart et al. |
| 5,602,449 A | 2/1997 | Krause et al. |
| 5,607,389 A | 3/1997 | Edwards et al. |
| 5,649,547 A | 7/1997 | Ritchart et al. |
| 5,653,718 A | 8/1997 | Yoon |
| 5,674,184 A | 10/1997 | Hassler, Jr. |
| 5,676,663 A | 10/1997 | Kim |
| 5,683,384 A | 11/1997 | Gough et al. |
| 5,687,739 A | 11/1997 | McPherson et al. |
| 5,769,086 A * | 6/1998 | Ritchart ............ A61B 10/0275 600/566 |
| 5,772,660 A | 6/1998 | Young et al. |
| 5,775,333 A | 7/1998 | Burbank et al. |
| 5,782,764 A | 7/1998 | Werne |
| 5,782,775 A | 7/1998 | Milliman et al. |
| 5,794,626 A | 8/1998 | Kieturakis |
| 5,797,907 A | 8/1998 | Clement |
| 5,810,806 A | 9/1998 | Ritchart et al. |
| 5,814,044 A | 9/1998 | Hooven |
| 5,823,970 A | 10/1998 | Terwilliger |
| 5,846,513 A | 12/1998 | Carroll et al. |
| 5,848,978 A | 12/1998 | Cecchi |
| 5,857,981 A | 1/1999 | Bucalo et al. |
| 5,857,982 A | 1/1999 | Milliman et al. |
| 5,871,454 A | 2/1999 | Majlessi |
| 5,873,886 A | 2/1999 | Larsen et al. |
| 5,876,340 A | 3/1999 | Tu et al. |
| 5,882,316 A | 3/1999 | Chu et al. |
| 5,897,567 A | 4/1999 | Ressemann et al. |
| 5,902,272 A | 5/1999 | Eggers et al. |
| 5,913,857 A | 6/1999 | Ritchart et al. |
| 5,925,044 A | 7/1999 | Hoffman et al. |
| 5,928,164 A | 7/1999 | Burbank et al. |
| 5,947,964 A | 9/1999 | Eggers et al. |
| 5,954,670 A | 9/1999 | Baker |
| 5,964,716 A | 10/1999 | Gregoire et al. |
| 5,980,469 A | 11/1999 | Burbank et al. |
| 5,984,919 A | 11/1999 | Hilal et al. |
| 5,997,560 A * | 12/1999 | Miller ............. A61B 17/32002 604/22 |
| 6,036,681 A | 3/2000 | Hooven |
| 6,050,955 A | 4/2000 | Bryan et al. |
| 6,056,700 A | 5/2000 | Burney et al. |

(56) References Cited

U.S. PATENT DOCUMENTS

| | | | |
|---|---|---|---|
| 6,077,230 A | 6/2000 | Gregoire et al. | |
| 6,086,543 A * | 7/2000 | Anderson | A61B 10/0233 600/567 |
| 6,120,462 A | 9/2000 | Hibner et al. | |
| 6,142,955 A | 11/2000 | Farascioni et al. | |
| 6,156,049 A | 12/2000 | Lovato et al. | |
| 6,176,865 B1 | 1/2001 | Mauze et al. | |
| 6,220,248 B1 | 4/2001 | Voegele et al. | |
| 6,231,522 B1 | 5/2001 | Voegele et al. | |
| 6,251,121 B1 | 6/2001 | Saadat | |
| 6,258,000 B1 | 7/2001 | Liechty, II | |
| 6,258,111 B1 | 7/2001 | Ross et al. | |
| 6,261,241 B1 | 7/2001 | Burbank et al. | |
| 6,261,302 B1 | 7/2001 | Voegele et al. | |
| 6,277,083 B1 | 8/2001 | Eggers et al. | |
| 6,312,429 B1 | 11/2001 | Burbank et al. | |
| 6,331,166 B1 | 12/2001 | Burbank et al. | |
| 6,344,026 B1 | 2/2002 | Burbank et al. | |
| 6,350,244 B1 | 2/2002 | Fisher | |
| 6,428,487 B1 | 8/2002 | Burdorff et al. | |
| 6,454,727 B1 | 9/2002 | Burbank et al. | |
| 6,471,700 B1 | 10/2002 | Burbank et al. | |
| 6,494,881 B1 | 12/2002 | Bales et al. | |
| 6,514,215 B1 | 2/2003 | Ouchi | |
| 6,514,248 B1 | 2/2003 | Eggers et al. | |
| 6,540,695 B1 | 4/2003 | Burbank et al. | |
| 6,562,032 B1 | 5/2003 | Ellman et al. | |
| 6,575,991 B1 | 6/2003 | Chesbrough et al. | |
| 6,589,157 B2 | 7/2003 | Fontayne et al. | |
| 6,689,145 B2 | 2/2004 | Lee et al. | |
| 6,712,773 B1 | 3/2004 | Viola | |
| 6,712,775 B2 | 3/2004 | Burbank et al. | |
| 6,758,824 B1 * | 7/2004 | Miller | A61B 10/025 600/566 |
| 6,835,173 B2 | 12/2004 | Couvillon, Jr. | |
| 6,994,667 B2 | 2/2006 | Singh | |
| 7,226,424 B2 | 6/2007 | Ritchart et al. | |
| 7,452,357 B2 | 11/2008 | Vlegele et al. | |
| 7,601,125 B1 | 10/2009 | Kai | |
| 8,460,204 B2 | 6/2013 | Quick et al. | |
| 2001/0002250 A1 | 5/2001 | Burbank et al. | |
| 2002/0019596 A1 | 2/2002 | Eggers et al. | |
| 2002/0022768 A1 | 2/2002 | Utsui | |
| 2002/0077646 A1 | 6/2002 | Truwit et al. | |
| 2002/0105797 A1 | 8/2002 | Navid et al. | |
| 2002/0143270 A1 | 10/2002 | Miller | |
| 2003/0004407 A1 | 1/2003 | Carroll et al. | |
| 2003/0125639 A1 | 7/2003 | Fisher et al. | |
| 2003/0199760 A1 | 10/2003 | Curpen et al. | |
| 2003/0236471 A1 | 12/2003 | Fisher | |
| 2004/0019299 A1 | 1/2004 | Ritchart et al. | |
| 2004/0024304 A1 | 2/2004 | Foerster et al. | |
| 2004/0092980 A1 | 5/2004 | Cesarini et al. | |
| 2006/0217635 A1 | 9/2006 | McCombs et al. | |
| 2008/0114264 A1 | 5/2008 | Weikel, Jr. et al. | |
| 2008/0319342 A1 | 12/2008 | Shabaz et al. | |
| 2010/0106015 A1 | 4/2010 | Norris | |
| 2010/0106056 A1 | 4/2010 | Norris | |
| 2010/0268117 A1 | 10/2010 | Shabaz et al. | |
| 2014/0039344 A1 | 10/2010 | Shabaz et al. | |

FOREIGN PATENT DOCUMENTS

| | | |
|---|---|---|
| DE | 1225813 B | 9/1966 |
| DE | 19528440 A1 | 2/1997 |
| DE | 10066004 A1 | 12/2001 |
| EP | 0146699 A1 | 7/1985 |
| EP | 0255123 A2 | 2/1988 |
| EP | 0472368 A2 | 2/1992 |
| EP | 0509670 A2 | 10/1992 |
| EP | 0601709 A2 | 6/1994 |
| EP | 0769281 A2 | 4/1997 |
| EP | 0858774 A2 | 1/1998 |
| EP | 0919190 A2 | 6/1999 |
| EP | 0966925 A1 | 12/1999 |
| EP | 0970658 A1 | 1/2000 |
| EP | 1072288 A2 | 1/2001 |
| GB | 1571926 | 7/1980 |
| GB | 2311468 A | 10/1997 |
| WO | 9207500 A2 | 5/1992 |
| WO | 9313718 A1 | 7/1993 |
| WO | 9502370 A2 | 1/1995 |
| WO | 9502371 A2 | 1/1995 |
| WO | 9503843 A1 | 2/1995 |
| WO | 9729702 A1 | 8/1997 |
| WO | 9742887 | 11/1997 |
| WO | 9808441 A1 | 3/1998 |
| WO | 9843531 A1 | 10/1998 |
| WO | 9846147 A1 | 10/1998 |
| WO | 9944506 A1 | 9/1999 |
| WO | 0012009 A2 | 3/2000 |
| WO | 0016697 A2 | 3/2000 |
| WO | 0128631 A1 | 4/2001 |
| WO | 0149184 A2 | 7/2001 |
| WO | 0158505 A2 | 8/2001 |
| WO | 0222023 A1 | 3/2002 |
| WO | 02062227 A1 | 8/2002 |
| WO | 02074214 A1 | 9/2002 |
| WO | 2004052212 A1 | 6/2004 |
| WO | 2005020925 A2 | 3/2005 |
| WO | 2005063126 A2 | 7/2005 |
| WO | 2006049911 A1 | 5/2006 |

OTHER PUBLICATIONS

Micklos, Timothy J., Percutaneous Biopsy Techniques, Manual of Oncologic Therapeutics (1989/1990) pp. 39-42.

Whitman, et al., Coaxial Core Needle Biopsy Under Mammographic Guidance: Indications and Applications, AJR:171, Jul. 1998, pp. 67-70.

International Search Report for PCT/US2005/027071 dated Mar. 21, 2006.

Written Opinion for PCT/US2005/027071 dated Mar. 21, 2006.

Written Opinion of the International Searching Authority for PCT/US2005/027071 dated Jul. 5, 2006.

International Search Report for PCT/US2005/027071 dated Jul. 5, 2006.

Written Opinion of the International Searching Authority for PCT/US2004/043021 dated Jul. 26, 2005.

International Preliminary Examination Report on Patentability for international application No. PCT/US/27071, dated Nov. 14, 2008.

Invitation to Pay Additional Fees, which includes Annex to Form PCT/ISA/206 Communication Relating to the Results of the Partial International Search for PCT/US2005/027071 dated Dec. 2, 2005.

Invitation to Pay Additional Fees, which includes Annex to Form PCT/ISA/206 Communication Relating to the Results of the Partial International Search for PCT/US2004/043021 dated Apr. 27, 2005.

Notification of Transmittal of the International Search Report and the Written Opinion of the International Searching Authority, or the Declaration for PCT/US2004/043021 dated Jul. 26, 2005.

* cited by examiner

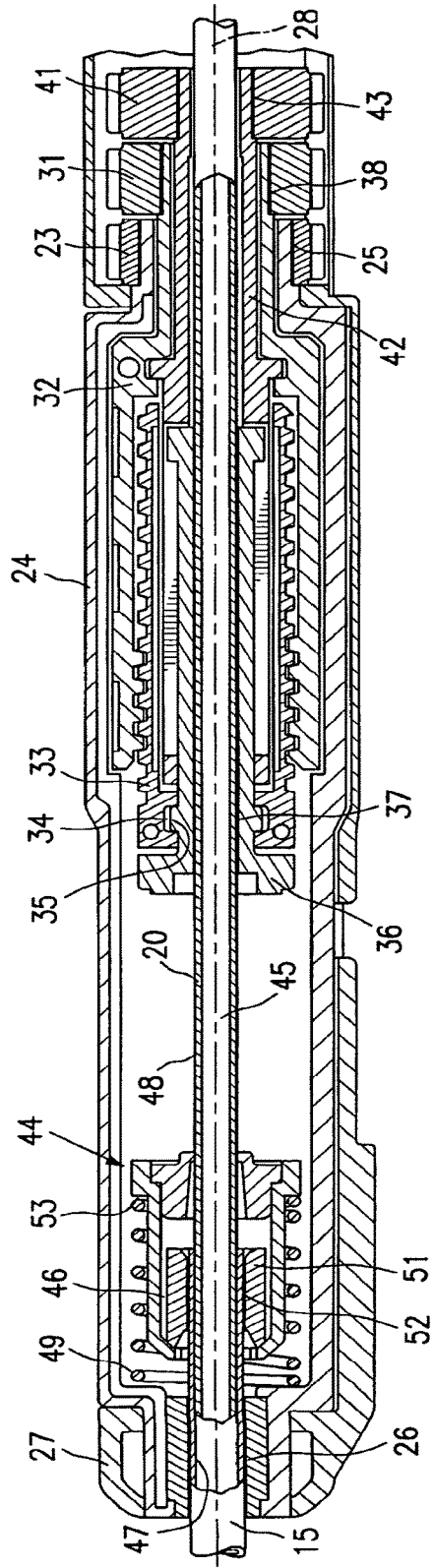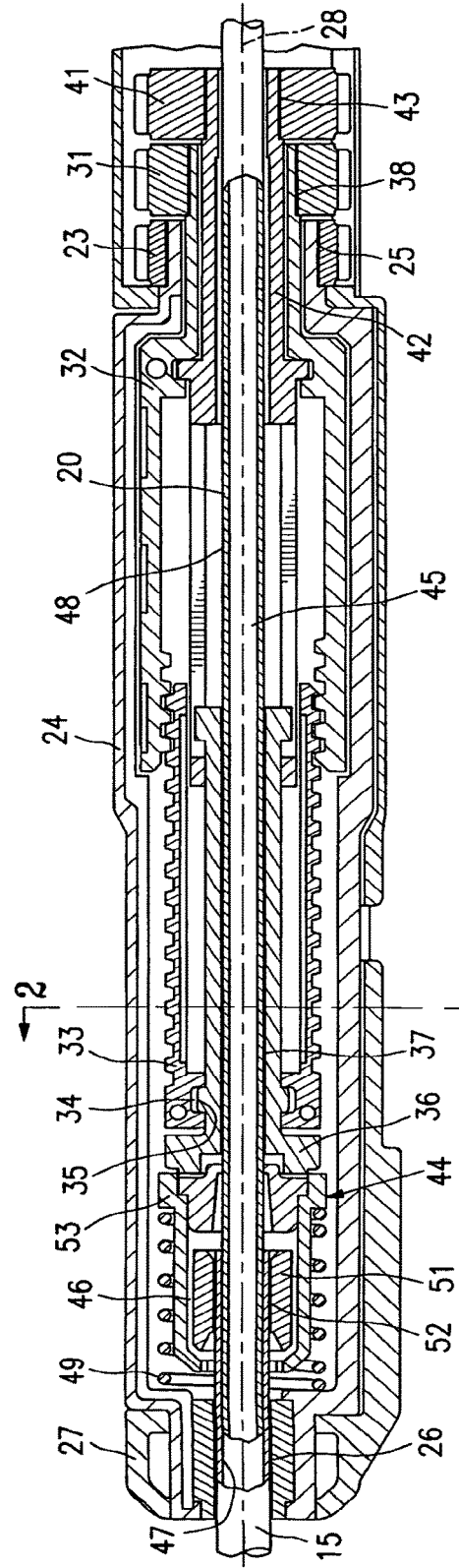
FIG. 4A
FIG. 4B

BIOPSY DEVICE WITH SELECTABLE TISSUE RECEIVING APERATURE ORIENTATION AND SITE ILLUMINATION

RELATED APPLICATIONS

This application is a continuation of application Ser. No. 12/229,545, filed Aug. 25, 2008, now U.S. Pat. No. 9,044,215, which is a divisional of application Ser. No. 10/911,106, filed Aug. 3, 2004, now U.S. Pat. No. 8,282,573, which is a continuation-in-part of application Ser. No. 10/642,406, filed Aug. 15, 2003, now U.S. Pat. No. 7,819,819, which is a continuation-in-part of application Ser. No. 10/374,915, filed on Feb. 24, 2003, now U.S. Pat. No. 7,189,206, all of which are incorporated herein by reference in their entirety and from which priority is claimed. This application is also related to application Ser. No. 12/229,553, filed Aug. 25, 2008, which is incorporated herein by reference in its entirety.

FIELD OF THE INVENTION

The present invention relates generally to tissue removing devices such as biopsy devices and the methods of using such devices. More specifically, it is directed to a device and method for accessing and removing pathologically suspect tissue from within a patient's body.

BACKGROUND OF THE INVENTION

In diagnosing and treating certain medical conditions, such as potentially cancerous tumors, it is usually desirable to perform a biopsy, in which a specimen of the suspicious tissue is removed for pathological examination and analysis. In many instances, the suspicious tissue is located in a subcutaneous site, such as inside a human breast. To minimize surgical intrusion into the patient's body, it is desirable to be able to insert a small instrument into the patient's body to access the targeted site and to extract the biopsy specimen therefrom.

Electrosurgical techniques have been used in a variety of biopsy procedures. In electrosurgery, high frequency electrical energy is typically applied to patient tissue through an active electrode, the electrical circuit being completed by a return electrode in contact with the patient's tissue. Electrical energy flowing through the tissue from the active electrode is effective to ablate tissue near the active electrode, forming an opening in the tissue and so allowing insertion of the instrument into a patient's body. A return electrode may be placed on the exterior of the patient's body or may be incorporated into the device itself. The return electrode is typically attached to the patient at a point remote from where the primary or active electrode contacts the tissue. However, in the case of a bipolar electrode for example, the return electrode may be disposed near to the active electrode. An electrosurgical biopsy instrument is disclosed and claimed in U.S. patent application Ser. No. 09/159,467 for "Electrosurgical Biopsy Device and Method," now U.S. Pat. No. 6,261,241, assigned to the assignee of the present application, and which is hereby incorporated by reference in its entirety.

While these electrosurgical biopsy devices have been found to be effective in many instances, they may not always be suitable for use in conjunction with magnetic resonance imaging.

SUMMARY OF THE INVENTION

This invention is directed to devices for accessing and severing tissue from a target site within a patient and methods for utilizing such devices. The devices embodying features of the invention provide access to a targeted tissue site within a patient and provide for the selection, separation and capture of a tissue specimen from supporting tissue at the targeted site.

A tissue collection device and system having features of the invention generally include an elongated, preferably disposable probe component having a plurality of operative elements and a driver component configured to receive the elongated probe component and drive the various operative elements of the probe component.

The elongated probe component has a distal shaft portion with a tissue penetrating distal tip, a tubular section proximal to the distal tip, an inner lumen extending within the tubular section and an open, tissue receiving aperture in the tubular section which provides access to tissue at the targeted site. The probe component includes an elongated tissue-cutting member, which is preferably at least in part cylindrically shaped. The tissue cutting member is provided with at least one tissue cutting edge which is configured to sever tissue extending into the interior of the tubular section through the aperture thereof. The cutting edge on the tissue cutting member may be configured for longitudinal cutting movement and may include oscillating rotational motion and/or reciprocating longitudinal motion to sever specimen tissue extending through the aperture from supporting tissue at the targeted site. The cutting surfaces or edges are radially spaced from a longitudinal axis of the probe component and are generally transversely oriented with respect to the longitudinal axis. The tissue cutter is preferably slidably disposed within the inner lumen of the tubular section, although it may be disposed about the tubular section. The probe component may also have a handle which releasably engages the driver component.

In one embodiment of the invention, the cutting member has an inner lumen preferably extending to the proximal end thereof for tissue specimen removal. While mechanical withdrawal of the tissue specimen may be employed, it is preferred to provide a vacuum within the cutting member from the proximal end of the cutting member. The proximal end of the cutting member may be configured to be in fluid communication with a vacuum source to aspirate the severed tissue specimen through the inner lumen of the cutting member to a tissue collection station. A higher fluid pressure may be maintained in the inner lumen of the cutting member distal to the tissue specimen to aid in transporting the specimen proximally through the inner lumen. In this manner, the mechanical withdrawal and/or the vacuum on the proximal end of the specimen and a higher pressure on the distal end of the specimen can move the specimen through the inner lumen of the cutting member to a tissue collection station.

In at least one embodiment, the handle of the probe component is secured, preferably releasably secured, to the driver housing provided to operably connect the various operative elements of the probe with operative elements of the driver component. The tissue cutting member is operatively connected to at least one driver to provide the desired cutting motion. The proximal end of the tubular section is rotatably secured within the handle housing so that the orientation thereof with respect to the longitudinal axis and therefore the orientation of the tissue receiving aperture within the tubular section, can be selected. The orientation of the aperture may be selected manually such as described in copending application Ser. No. 10/642,406, filed February August 15, 2003 or it may be preset or selected electronically by a control module which also controls the operation of the cutting member and electrical power. The aperture orientation setting may be selected before or after the distal portion of the probe component is inserted into the patient.

The driver component has at least two and preferably three driver units for operating the probe component secured to the driver component. Specifically, the driver component has a first driver unit for rotating the tubular section of the probe component, a second driver unit for moving the cutting member along a longitudinal axis of the cutting member and optionally a third driving unit for rotating or oscillating the cutting member about the longitudinal axis. The first driver unit rotates the tubular section of the probe component, preferably in discrete steps, so that the location of the tissue receiving aperture in the distal extremity of the tubular section can be selected prior to or during the procedure. The discrete rotational steps of the tubular section are preferably in 30° or multiples thereof so that the rotational movement will follow 12 hour clock markings. Preferably, the second and third driver units are operable together so that the cutting member may rotate or oscillate about a longitudinal axis as the cutter member is moved longitudinally. This allows a rotation or an oscillation of the cutter during the cutting process which can aid in cutting tissue.

The driver component may have one or more light sources in a distal portion thereof to illuminate the accessing site during the procedure.

A method of cutting and collecting a tissue specimen with a tissue collection device embodying features of the invention includes advancing such a device at least partially into tissue at a desired site within the patient's body with the tissue penetrating distal tip of the outer cannula disposed distal to the tissue specimen to be separated from the target site. A vacuum is established within the inner lumen of the tubular section to draw tissue through the aperture therein into the inner lumen of the tubular section. The cutting member, which is slidable disposed within the inner lumen of the tubular section, may then be moved longitudinally to cut a tissue specimen from supporting tissue at the target site by the longitudinal motion, which preferably includes oscillating rotational movement and/or reciprocating longitudinal movement. The vacuum established within the inner lumen of the tubular section may be applied through the inner lumen of the tissue cutting member when the tissue cutting member is disposed within the tubular section. The applied vacuum within the inner lumen of the tissue cutting member, may also be utilized to pull or aspirate the separated tissue sample proximally. In addition, or alternatively, a higher fluid pressure may be maintained in a distal part of the inner lumen of the tubular section, distal to the specimen, to push the tissue specimen proximally, Alternatively, the tissue specimen may be mechanically withdrawn. Fluid pressure may include pressure from a liquid delivered into the interior of the device, such as a physiological saline solution, and may include a gas, such as pressurized carbon dioxide, nitrogen or air, delivered into the interior of the device. Access to ambient air can also maintain a sufficiently high pressure differential to move the specimen through the inner lumen of the cutting member. Anesthetic may be injected to the target site through the outer cannula or the inner lumen of the cutting member. Upon removal from the patient, the tissue specimen may then be subjected to pathological examination. After acquisition of a tissue specimen or specimens, the tissue separation system may be repositioned for further tissue separation and collection or it may be withdrawn from the patient.

The tubular section of the probe provides the support for the probe to enable precise location of the accessing port to the desired location at the target site with its radial orientations being preset before the device is introduced into the patient or selected after the tubular section is disposed within the patient. The cutting member quickly and cleanly severs the tissue specimen drawn into the interior of the tubular section though the aperture by the action of the vacuum or otherwise. Upon removal of the tissue specimen, the tissue receiving aperture may be radially repositioned about the longitudinal axis of the tubular section of the probe component so that a plurality of specimens may be taken from the target site. The orientation of the tissue receiving aperture during the procedure may follow a preselected pattern or may be selected by the physician for other selected tissue specimens.

A tissue acquisition system assembly embodying features of the invention may include a device for delivery of one or more marker bodies through a tubular member of a biopsy device such as the tubular cutting member. Such a marker delivery device includes an elongated shaft having an inner lumen and a discharge opening in a distal portion of the elongated shaft, at least one marker body which is disposed within the inner lumen of the elongated shaft, a pusher element which is slidably disposed within the delivery device and which is configured to urge at least one marker body out the discharge opening in the distal portion of the elongated shaft. The marker delivery device has a distally flared guide member which is slidably disposed on the elongated shaft to guide the distal portion of the elongated shaft into a proximal end of the tubular member of a biopsy device.

These and other advantages of the invention will become more apparent from the following detailed description of the invention and the accompanying exemplary drawings.

BRIEF DESCRIPTION OF THE DRAWINGS

FIG. 4A is a longitudinal cross-section of the probe shown in FIG. 3 taken along the lines 4-4 with the tissue cutting element in a withdrawn position.

FIG. 4B is a longitudinal cross-section of the probe shown in FIG. 3 taken along the lines 4-4 with the tissue cutting element in a forward or closed position.

DETAILED DESCRIPTION OF EMBODIMENTS OF THE INVENTION

Figure 1:
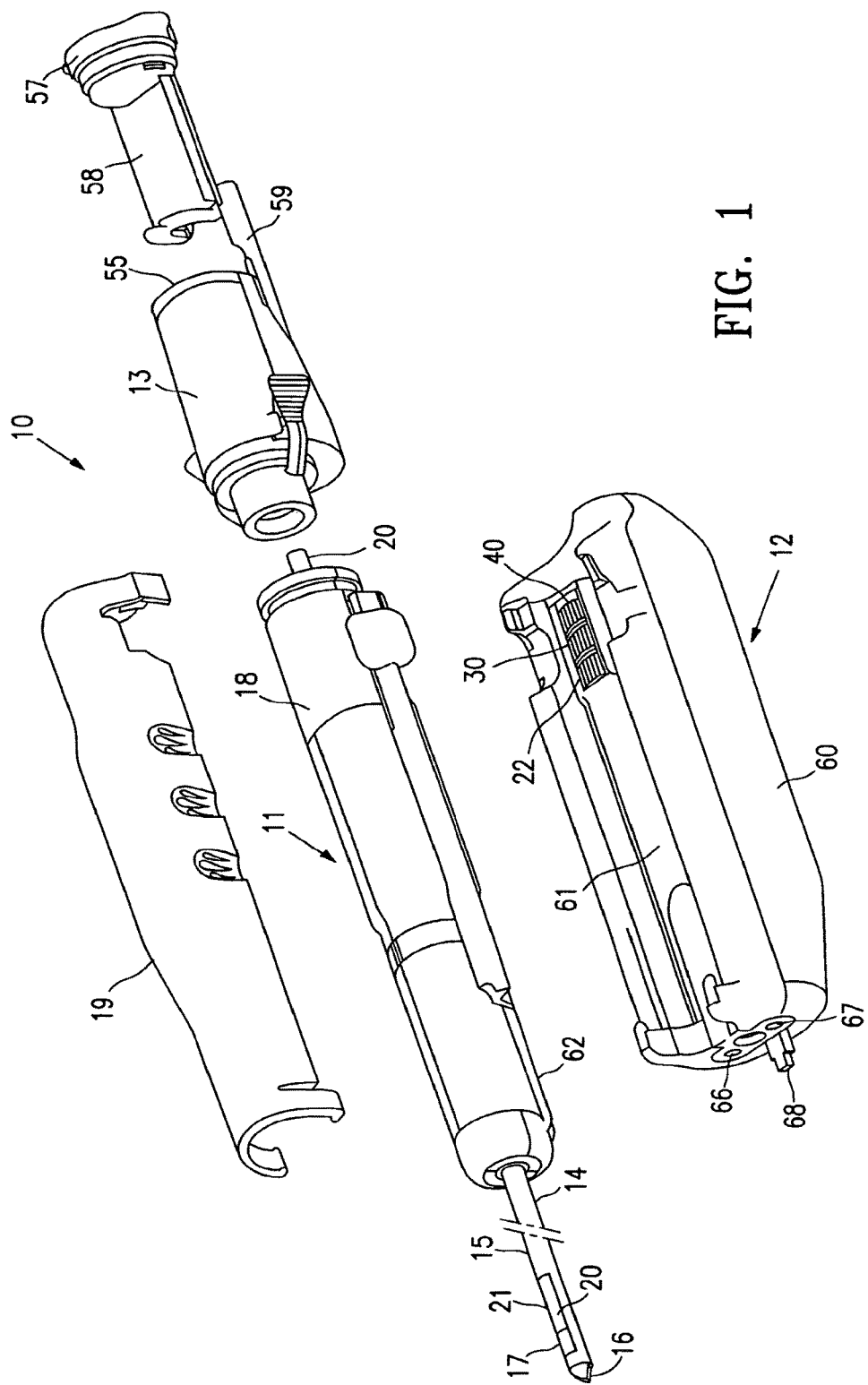
FIG. 1 is an exploded view of the elongated tissue biopsy system embodying features of the invention.
Figure 2:
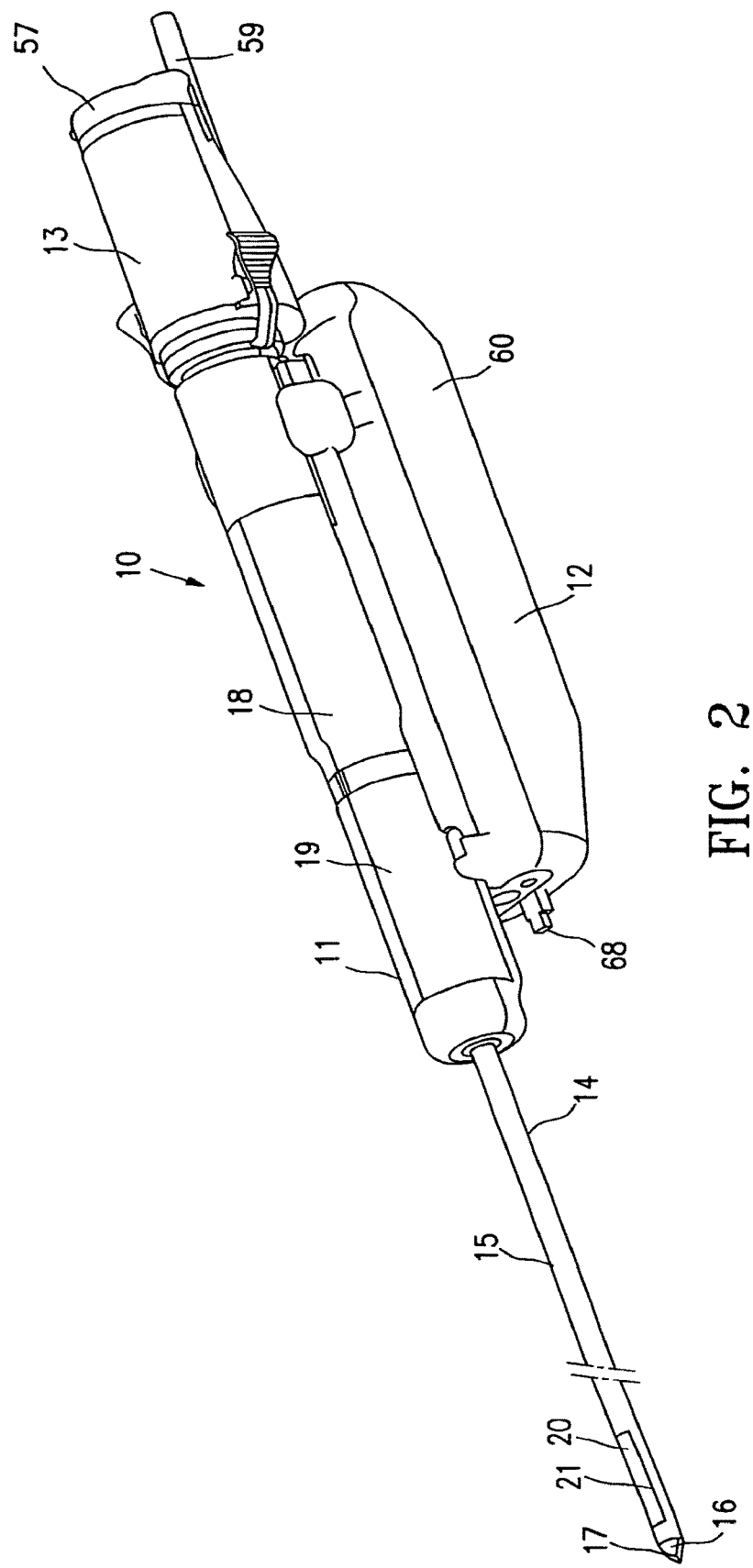
FIG. 2 is a perspective view of the embodiment shown in FIG. 1 in an assembled condition without a housing cover for the probe component.
Figure 3:
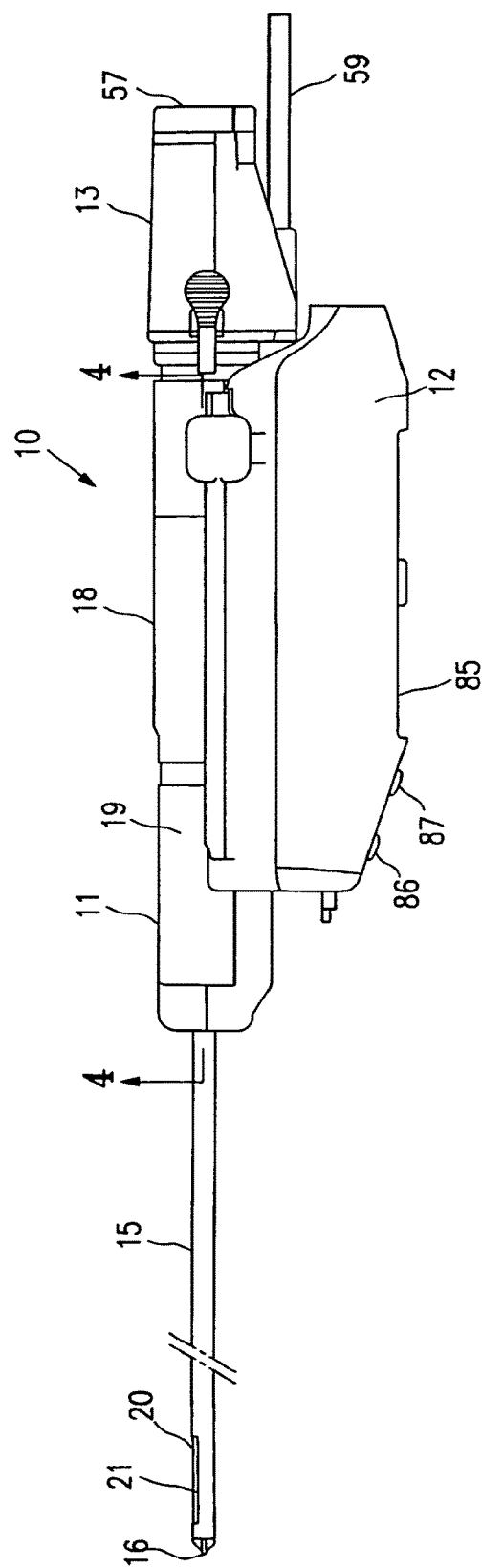
FIG. 3 is a side elevational view of the tissue biopsy device shown in the FIG. 2.
Figure 5:
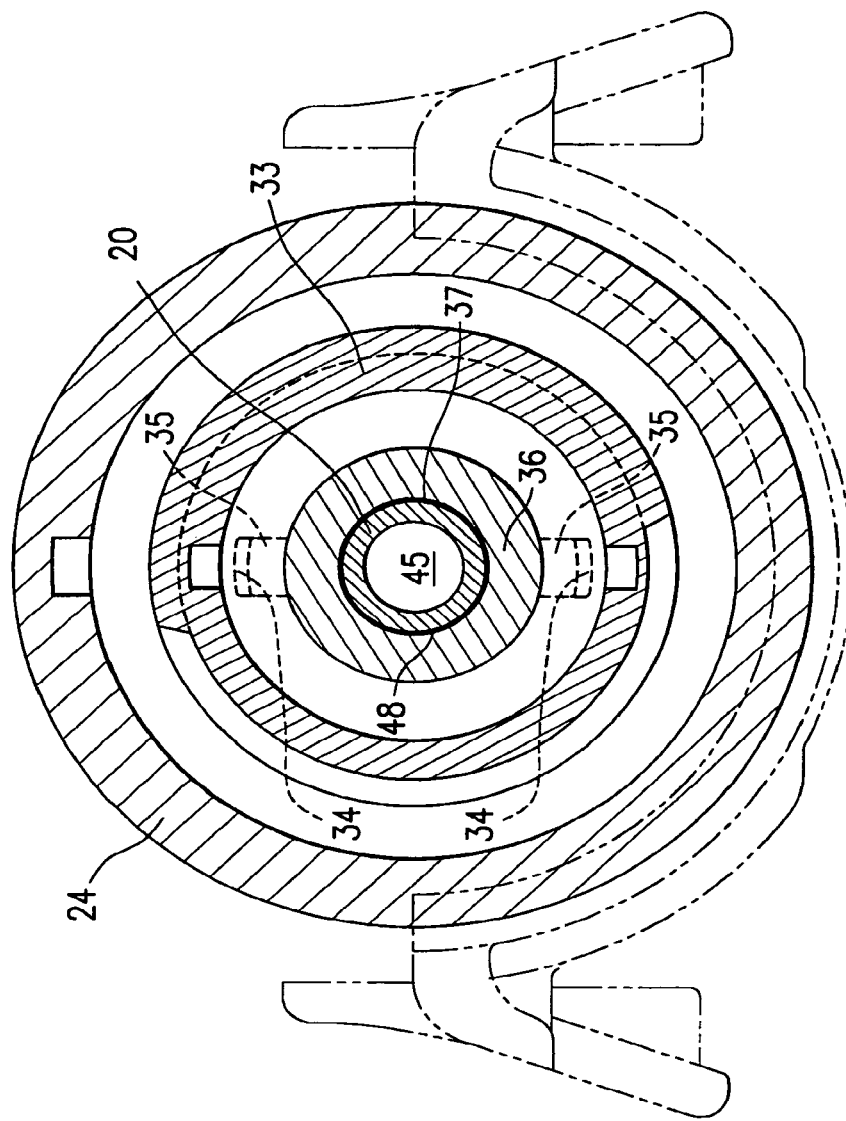
FIG. 5 is a transverse cross-sectional view of the probe shown in FIG. 4B taken along the lines 5-5.
Figure 6:
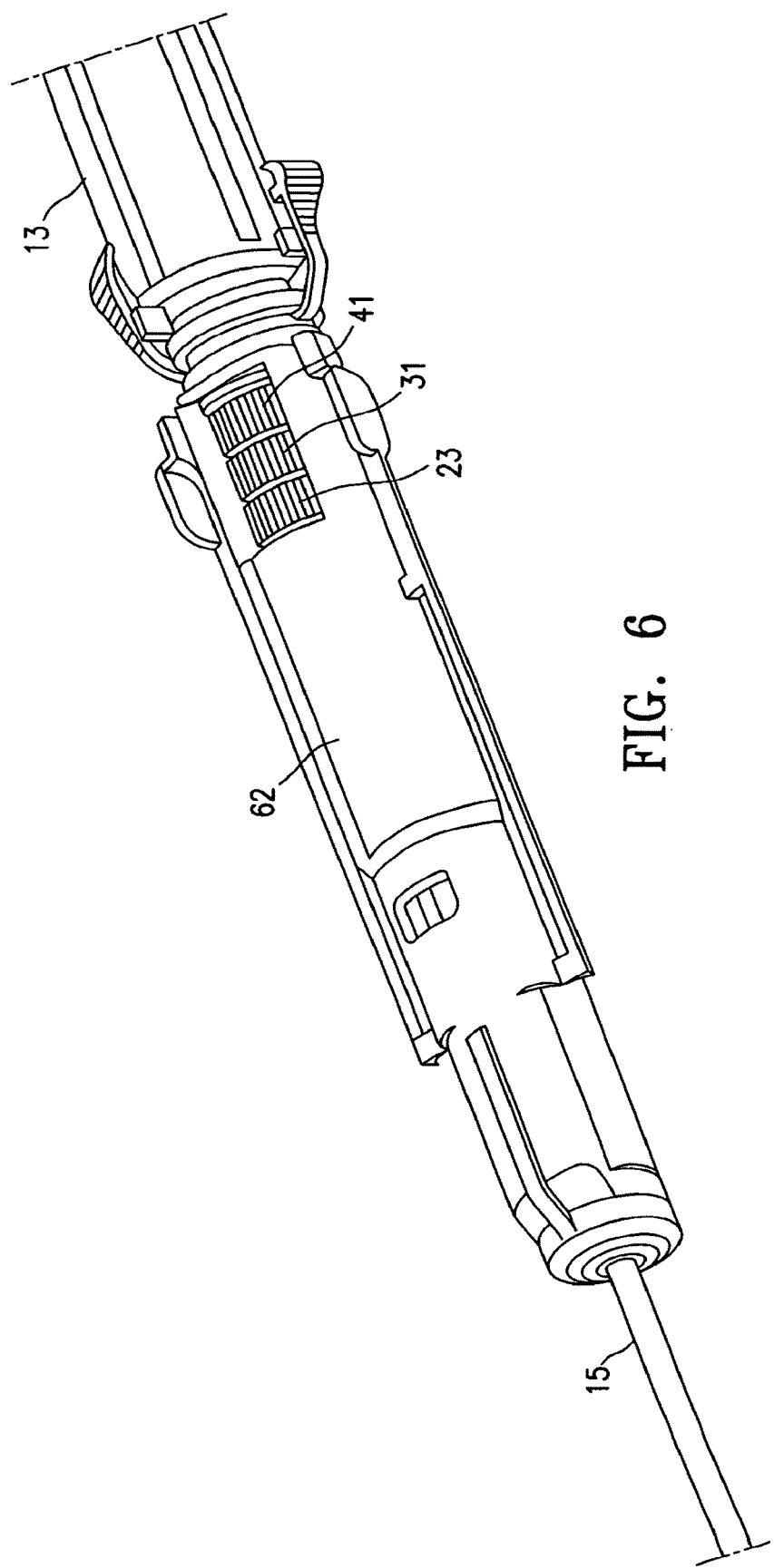
FIG. 6 is a perspective view of the underside of the probe shown in FIG. 1.

FIGS. 1-3 illustrate a biopsy system 10 embodying features of the invention which includes a disposable probe component 11, a driver component 12 and specimen collector 13.

The probe component 11 generally includes an elongated distal shaft 14 having a tubular section or cannula 15 with a tissue penetrating tip 16 on the distal end thereof and an open, tissue receiving aperture 17. The probe component 11 also includes a probe housing 18 with a housing cover 19 which is configured to interfit with the driver component 12. A tissue cutter 20 is slidably disposed within the probe and has a distal cutting surface 21 which severs tissue which extends through the tissue receiving aperture 17.

Details of the probe component 11 are further shown in FIGS. 4A and 4B. The probe housing 18 has a mechanical system for rotating the housing and the tubular section 15 secured thereto to control the angular position of the tissue receiving aperture 17 and for moving the tissue cutter 20 slidably disposed within the probe component 11.

Figure 8:
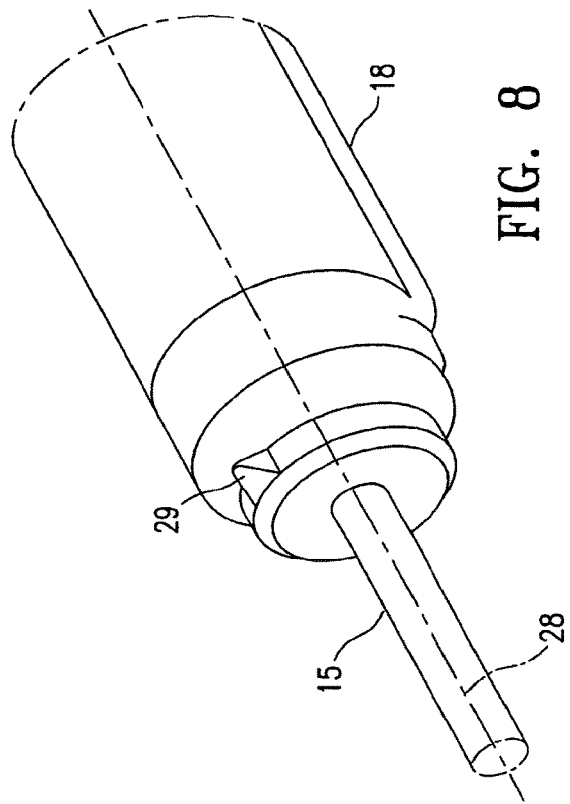
FIG. 8 is an enlarged perspective view of the distal end of the probe housing illustrating a marker element which depicts the orientation of the aperture in the tubular section of the biopsy device.

The mechanical system of the driver component 12 has first driving gear 22 that is configured to engage the probe gear 23 and rotate the probe housing 18 so as to adjust the orientation of aperture 17 in the distal extremity of the tubular section 15. The probe gear 23 is secured to the rotating connector body 24 by adhesive 25. The proximal extremity of the tubular section 15 is secured to the rotating connector body 24 by adhesive 26. An end cap 27 retains the connector body 24 within the probe housing 18. Rotation of the probe gear 23 rotates the connector body 24 and the attached tubular section 15. The rotation is preferably controlled so that the tubular section 15 rotates in discrete steps about the longitudinal axis 28 to adjust the angular orientation of the aperture 17 about the longitudinal axis. Preferably these discrete orientations may be provided in increments of 30° which can be readily indicated by arrow 29 at the distal end of the probe housing 18 as shown in FIG. 8.

The second driving gear 30 is configured to drive the tissue cutter 20 longitudinally. The driving gear 30 engages probe gear 31 which drives cutter traverse nut 32 and cutter screw 33 threadably connected to the cutter traverse nut. The distal end of the cutter screw 33 is provided with a recess 34 which receives the rib 35 of the cutter shuttle 36. The cutter shuttle 36 is secured to the tissue cutter 20 by adhesive 37. The probe gear 31 is secured to the cutter traverse nut 32 by adhesive 38. Rotation of the probe gear 31 adjusts the relative axial position of the cutter screw 33 with respect to the cutter traverse nut 32 which is secured to the cutter shuttle 36. Longitudinal movement of the tissue cutter 20 follows the longitudinal movement of the cutter shuttle 36 resulting from the movement of cutter screw 33. The length of the tissue receiving aperture 17, and as a result the length of the specimen, can be controlled by adjusting the initial longitudinal position of the distal end of the tissue cutter 20 within the aperture, before cutting.

The third driving gear 40 is configured to rotate or oscillate the tissue cutter 20 as the cutter moves along the longitudinal axis 28 to facilitate the cutting action of the cutting surface 21 on the distal end of the cutter. The third driving gear 40 engages probe gear 41 which is secured to cutter oscillation shaft 42 by adhesive 43. The probe gear 41 may be oscillated back and forth about the longitudinal axis 28 or rotated continuously in a single direction about the longitudinal axis, or both depending upon the desired rotational movement of the tissue cutter.

A biased valve assembly 44 is provided in the distal end of the probe housing 18 to ensure sealing when a vacuum is developed within the interior 45 of the tissue cutter 20 while providing an atmospheric vent 46 between the interior surface 47 of the tubular section 15 and the exterior surface 48 of the tissue cutter 20. The valve assembly 44 includes a spring 49, valve body 50 and a valve collar 51 which is secured to the proximal end of the tubular section 15 by adhesive 52. The proximal end of the valve spring 49 rests against the shoulder 53 provided in the exterior of the valve body 50. A biased cutter shaft seal 54 slidably engages the exterior 48 of the tissue cutter 20.

The tissue specimen collector 13 is secured to the proximal end of the housing of probe component 11 and has an interior 55 in fluid communication with the inner lumen 56 extending within the tissue cutter 20 and has a removable proximal wall 57 of specimen receiving cartridge 58 which gives access to the interior 55 and any tissue specimens which may have been drawn therein. A vacuum is generated within the interior 55 to draw tissue specimens through the inner lumen 45 into the interior 55. Tubular member 59 has a distal end which is in fluid communication with the interior 55 of the tissue specimen collector 13 and has a proximal end (not shown) which is configured to be connected to a vacuum source. Application of a vacuum within the tubular member 59 aids in pulling tissue into the interior 17 of the tubular section 15 and transfer of the severed tissue specimen through the inner lumen 45 of the tissue cutter 20 to the specimen cartridge 58.

The driver 12 has a housing 60 with an upper concave surface 61 which is configured to receive the lower surface 62 of the probe housing 18. Three partially exposed driving gears 22, 30 and 40 are provided on the proximal end of the driver 12 which are configured to engage the probe gears 23, 31 and 41 respectively. The drive 12 is provided with three separately operating drive motors (not shown) which drive the drive gears 22, 30 and 40. The separate drive motors (not shown) are connected to and the operation thereof controlled by a control module, such as described in copending application Ser. No. 10/847,699, filed on May 17, 2004. The control module controls the motors which move the individual drive gears 22, 30 and 40. The gear 22 engages gear 23 in the probe 11 to control the rotation of the probe housing 18 and the location and orientation of the tissue receiving aperture 17. The drive gear 30 engages probe gear 31 to control the longitudinal position and motion of the tissue cutter 20 along the longitudinal axis 28. Drive gear 40 engages probe gear 41 to control the oscillation or rotation of the tissue cutter 20 about the longitudinal axis 28.

Figure 7:
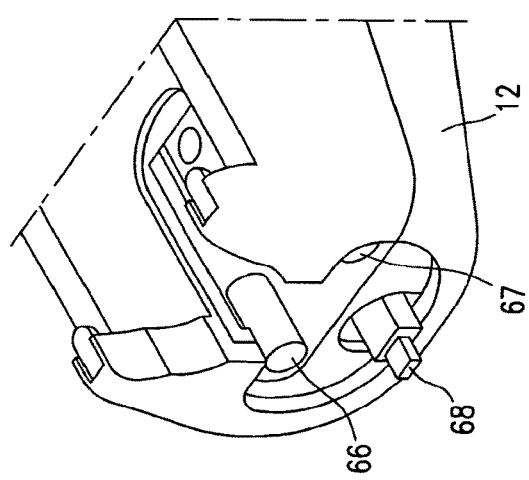
FIG. 7 is an enlarged perspective view of the distal end of the driver unit shown in FIG. 1.

As shown in FIG. 7, the front face of the driver component 12 is provided with light sources 66 and 67 and a manually activatable switch 68 to activate the light sources and enable the physician and other operating personnel to better view the operating site on the patient. Other manual switches, e.g. a foot activated switch, may be employed.

Alternatively, the light sources may be automatically activated when the probe component 11 is installed on the driver 12 or other events such as when electrical power is turned on. The driver component 12 may have a battery pack for the light sources 66 and 67.

The penetrating distal tip 16 may have a variety of tip shapes. A particularly suitable distal tip shape is described in provisional application Ser. No. 60/532,277, filed on Dec. 23, 2003. Alternatively, the distal tip may be provided with an arcuate RF electrode such as disclosed in U.S. Pat. Nos. 6,261,241, and 6,471,700, both assigned to the present assignee.

The separate driver component 12 allows the entire probe unit to be disposable. The drive gears of the drive component 12 control the motion of the tissue cutting member 20 for cutting and the motion of the tubular section 15 to orient the aperture 17. Other means (not shown) may provide mechanical and electrical power, vacuum, and control to the probe device. Examples of replaceable snap-in type probe units are disclosed in Burbank et al., U.S. patent application Ser. No. 10/179,933, "Apparatus and Methods for Accessing a Body Site" hereby incorporated by reference in its entirety. Drive units such as that described in WO 02/069808 (which corresponds to co-pending U.S. application Ser. No. 09/707, 022, filed Nov. 6, 2000 and U.S. application Ser. No. 09/864,021, filed May 23, 2001), which are assigned to the present assignee, may be readily modified by those skilled in the art to accommodate the movement of the cutting member 20.

The distal end of the probe component 11 is advanced within the patient with the tissue cutter 20 in a forward or closed position (FIG. 4B), until the aperture 17 of the tubular section 15 is located in a desired location for taking a tissue specimen. The tissue cutter 20 is then withdrawn proximally to an open position to open the aperture 17. The withdrawal of the tissue cutter can be used to control the length of the aperture which is opened in order to control the length of the specimen which is severed. A vacuum is applied to the interior 45 of the tissue cutter 20 to draw tissue at the site into the inner lumen of the tubular section 15 through the aperture 17. The tissue cutter 20 is then driven distally by rotation of probe gear 30 and rotated or oscillated by drive gear 40 engaging probe gear 41 to sever the aspirated tissue from the supporting tissue at the target site with the tissue cutting surface 21. The vacuum within the interior of the tissue cutter 20 causes the tissue specimen to be drawn through the inner lumen 45 of the tissue cutter 20 and into the cartridge 58 of specimen collector 13 shown in FIG. 2. Positive pressure or even ambient conditions distal to the tissue specimen can facilitate tissue passing through the interior 45 of tissue cutter 20. If another tissue specimen is desired, the tubular section 15 may be rotated by the drive gear 22 engaging the probe gear 23 in one or more steps to repeat obtaining another tissue specimen in the same manner without otherwise moving the probe component 11. Typically, a first tissue specimen is obtained with the aperture 17 of the probe 11 in the 12 o-clock position, the second at the 3 o-clock position, the third at the 9 o-clock position and the fourth at the 6 o-clock position. The location of the second and third specimens may be reversed. The position of the aperture 17 may be indicated by a marker arrow 29 at the end cap 27 so that the physician or other operating personnel can readily determine what the orientation of the aperture 17 within the patient.

Figure 9:
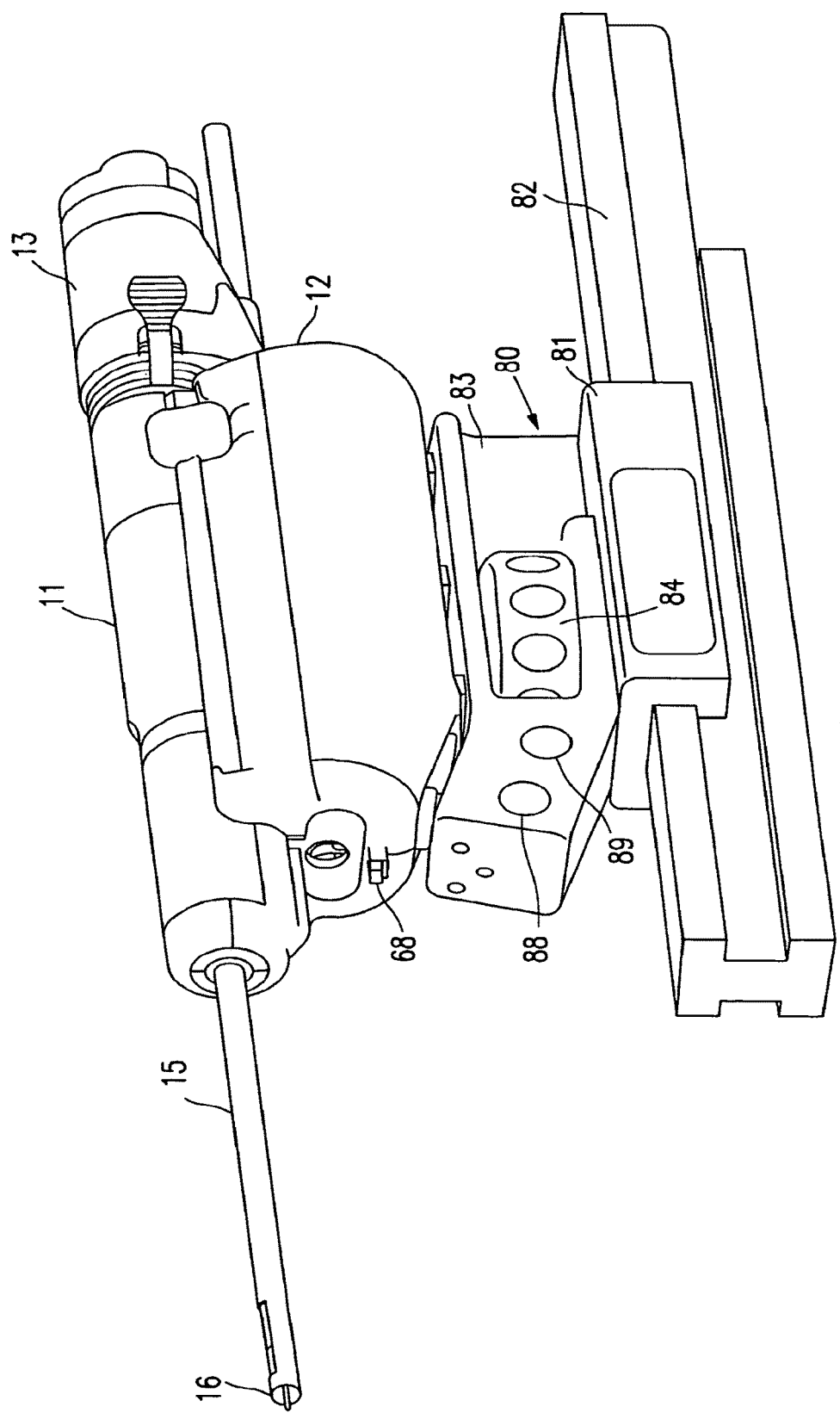
FIG. 9 is a perspective view of the tissue biopsy system shown in FIG. 1 assembled and mounted on a stereotactic frame.
Figure 10:
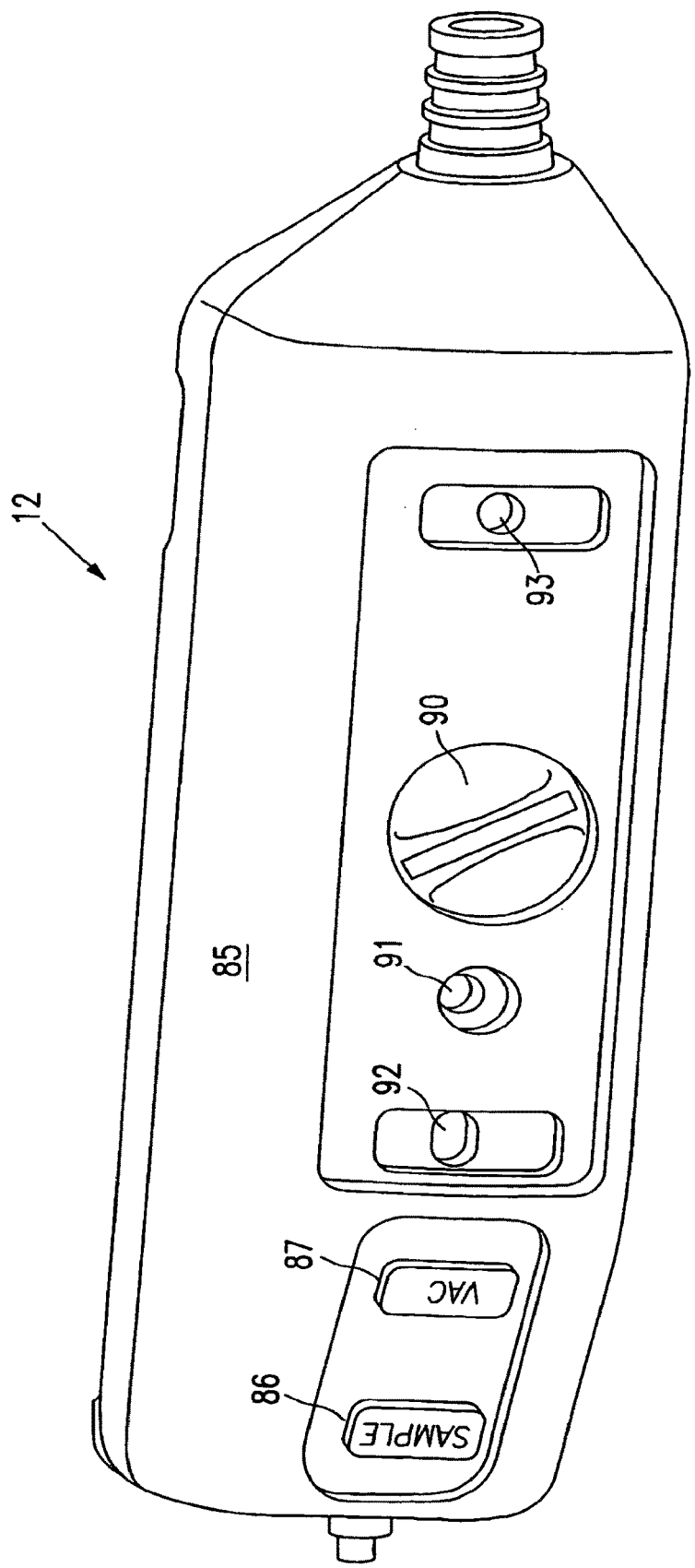
FIG. 10 is a perspective view of the underside of the driver shown in FIG. 1.

The biopsy system 10 may be hand held for some biopsy procedures or the system may be mounted on a stereotactic mounting stage 80 as shown in FIG. 9. A shoe 81 is slidably mounted to a rail 82 of a Fisher stage. The mounting member 83 is secured to the shoe 81 by a threaded post (not shown) secured to thumbwheel 84. As shown in FIG. 10, the bottom surface 85 of the driver component 12 is configured to conform at least in part to the upper surface of the mounting member 83. The sampling and vacuum switches 86 and 87 respectively on the driver component 12 are actuated by the optional sampling and vacuum actuating elements 88 and 89 on the mounting member 83. Alternatively, sampling and vacuum may be actuated with a foot pedal. As shown in FIG. 10, the driver component has an operator dial 90 which when turned opens a threaded hole 91 for receiving a threaded post (not shown) secured to the thumbwheel 84 and the locating pin holes 92 and 93 which receive the complementary posts (not shown) in the mounting member 83.

As mentioned above, positive pressure or even ambient conditions will aid in passing the severed tissue specimen through the inner lumen 45 of tissue cutter 20 into the cartridge 58 of specimen collector 13. As shown in FIGS. 4A and 4B venting valve can provide ambient pressure behind the tissue specimen in the cutter interior 45 from the interior of the tubular section 15. The valve body 50 is opened for atmospheric venting when the tissue cutter 20 is in the forward position upon the completion of severing the specimen from the tissue site. However, when the tissue cutter 20 is pulled back proximally the valve spring 49 urges the valve body 50 back to a closed position. While the tissue cutter 20 is shown with a tissue cutting surface 21 which is perpendicular to the longitudinal axis 28, the tissue cutting surface may be at an angle or even parallel to the longitudinal axis as described in co-pending application Ser. No. 10/642,406, filed Aug. 15, 2003.

The distal cutting edge 21 of the tissue cutter 20 may initially be located proximal to the aperture 17 to provide a full aperture for receiving tissue or it can be initially located within the aperture 17 in order to control the length of the specimen. The cutting action of tissue cutter 20 preferably continues until the beveled cutting surface 21 has completely traversed the aperture 17 to ensure that the tissue drawn through the aperture is completely severed from supporting tissue at the biopsy site. A vacuum may be applied to aspirate the severed tissue specimen through the inner lumen of the tissue cutter 20 to the cartridge in the specimen collector at the proximal end of the biopsy device. Positive pressure or access to ambient conditions may be provided in the distal end of the tubular section to aid in the specimen transfer.

After the removable wall 57 of the specimen receiving cartridge 58 is removed and the specimens therein removed, it is frequently desirable to deliver one or more markers to the target site from which the specimens have been removed. Such marker delivery devices are shown in co-pending application Ser. No. 10/753,694, filed on Jan. 7, 2004 and co-pending application Ser. No. 10/444,770, filed May 23, 2003. However, the distal ends of these marker delivery devices are very small and they can be difficult to insert into the proximal end of the tissue cutter 20 which is just slightly larger to accommodate the marker delivery shaft.

Figure 11:
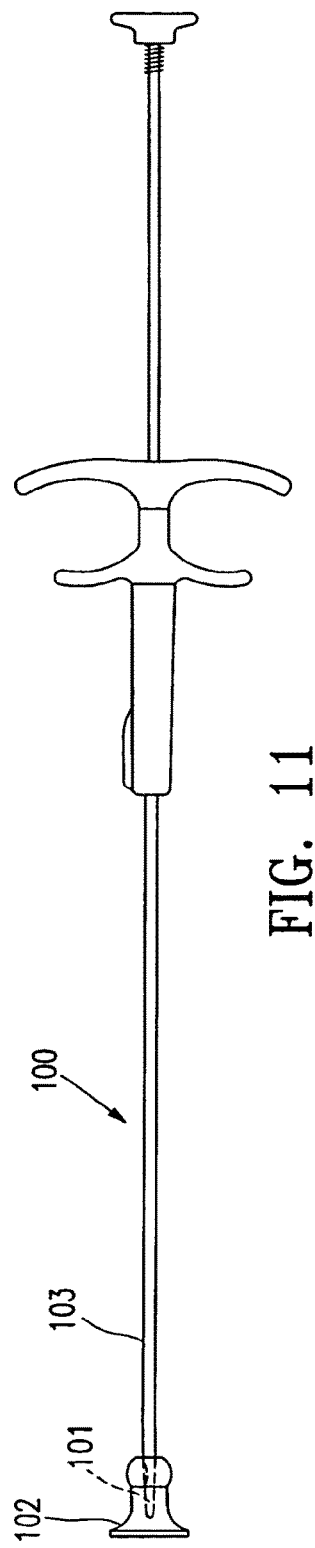
FIG. 11 is an elevational view of a marker delivery device with a flared guide on the distal end of the shaft which facilitates guiding the distal tip of a marker delivery device into the interior of the proximal end of the tissue cutter.
Figure 12:
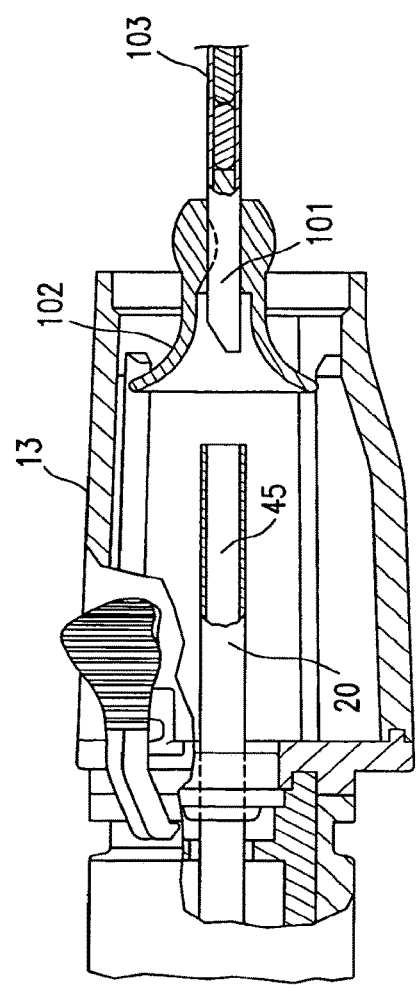
FIG. 12 is a longitudinal cross-sectional view of the distal end of the marker delivery device and flared guide disposed within the tissue collection component shown in FIG. 1.
Figure 13:
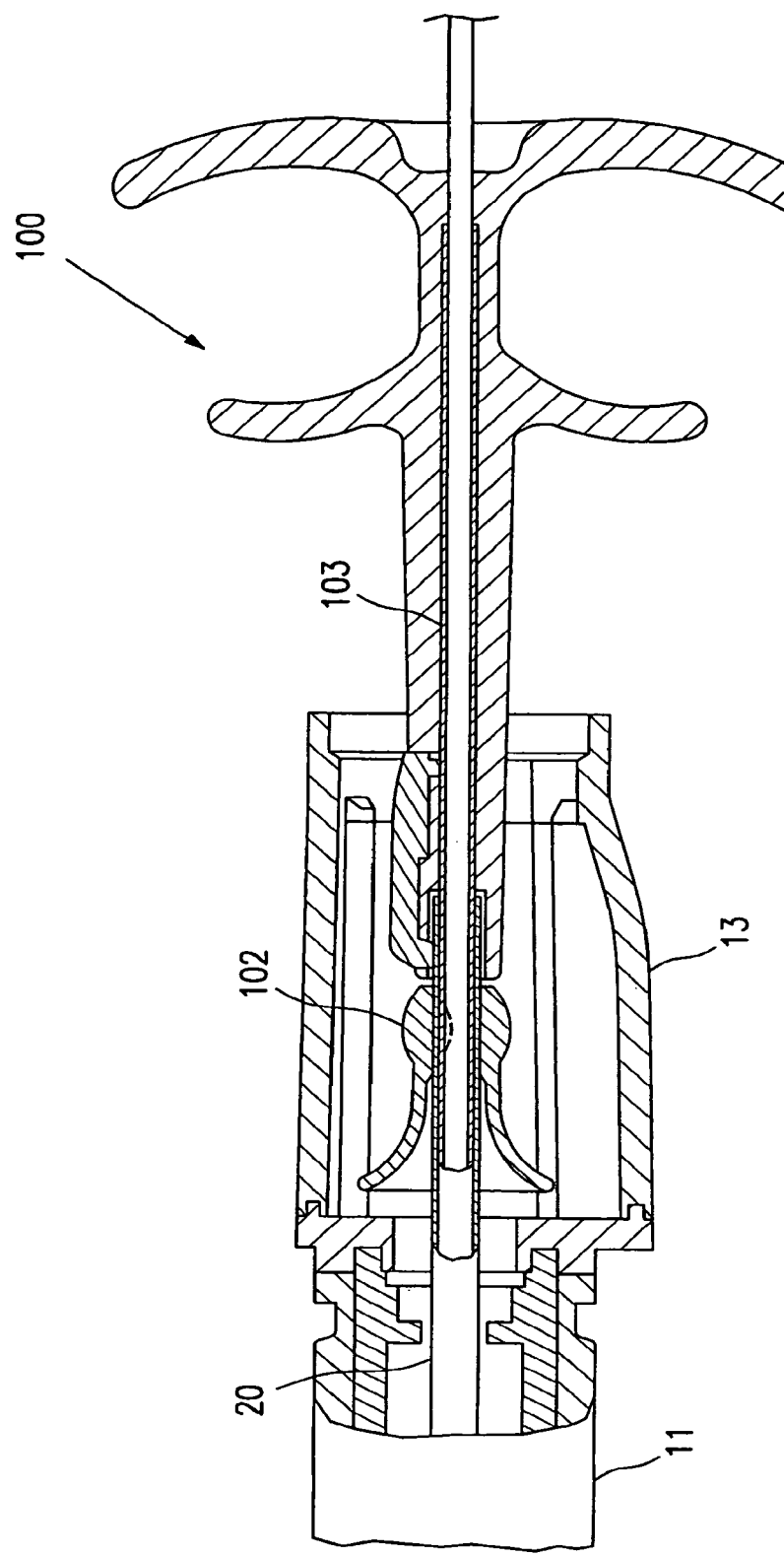
FIG. 13 is a longitudinal cross sectional view of the proximal end of the marker delivery device with the flared guide at the proximal end of the shaft and with the shaft deployed within the inner lumen of the tissue cutter.

FIG. 11 illustrates a marker delivery device 100 which is particularly suitable to facilitate the introduction of the distal end of the shaft 101 into the inner lumen 45 of the tissue cutter 20 and the advancement therein. As indicated into the inner lumen 45 of the tissue cutter 20 to eject one or more markers through the aperture 17 in the tubular section 15 before the biopsy device 10 is removed from the patient. As shown in FIG. 13, to aid in the insertion of the small diameter distal tip 101 of a marker delivery device 100 into the slightly larger inner lumen 45 of the tubular cutter 20 at its proximal end, the distal tip is preferably provided with an outwardly flared guide 102 which is slidably mounted on the shaft 103 of the marker delivery device 100. The proximal end of the tubular cutter 20, the flared guide 102 and/or the distal tip 101 may be provided with mating guide elements which orient the marker delivery device so that one or more markers are discharged through the aperture 17 when the pusher element slidably disposed within the delivery device is urged distally to press at least one marker body out the discharge opening in the distal portion of the elongated shaft of the marker delivery device. The delivery of markers to the target site after specimen removal, while the distal end of the biopsy device is still at the biopsy site, ensures that the markers are properly position at the biopsy site. While the slidably mounted, flared proximal guide 102 is described with respect to being disposed on the shaft 103 of marker delivery device 101, the flared guide 102 has wide application within a variety of biopsy and other devices where one small diameter tubular member is to be inserted into a slightly larger, but still small diameter second tubular member.

The elongated probe component 11 of the biopsy system 10 has a length of about 3 to about 20 cm, preferably, about 5 to about 13 cm, and more specifically, about 8 to about 9 cm for breast biopsy use. To assist in properly locating the probe 11 during advancement thereof into a patient's body, the distal extremity of the tubular section may be provided with a marker at a desirable location that provide enhanced visualization by eye, by ultrasound, by X-ray, MRI or other imaging or visualization means. Manual palpation may also be employed. An echogenic polymer coating that increases contrast resolution in ultrasound imaging devices (such as ECHOCOAT™ by STS Biopolymers, of Henrietta, N.Y.) is suitable for ultrasonic visualization. Radiopaque markers may be made with, for example, stainless steel, platinum, gold, iridium, tantalum, tungsten, silver, rhodium, nickel, bismuth, other radiopaque metals, alloys and oxides of these metals. In addition, the surfaces of the device in contact with tissue or other components of the device may be provided with a suitable lubricious coating such as a hydrophilic material or a fluoropolymer.

The tubular section and the tissue cutter are preferably formed of a surgical grade stainless steel. However, other high strength materials such as MP35N, other cobalt-chromium alloys, NiTi alloys, ceramics, glasses, and high strength polymeric materials or combinations thereof may be suitable.

A patient's skin usually must be breached in order to gain access to a body site where a tissue specimen is to be obtained. A scalpel or other surgical instrument may be used to make an initial incision in the skin. After the specimens have been taken, the biopsy device may be removed from the patient. The entire device may be removed; however, in some embodiments, the cartridge 58 may be removed from the system 10 and a delivery cannula may be inserted through the inner lumen of the cutter 20 to deliver markers to the biopsy site through the aperture 17. In addition, it will be readily appreciated that other types of instruments may be inserted into the tissue site through the tissue cutter in addition to or in place of the instruments described above. Moreover, therapeutic or diagnostic agents may be delivered through the tissue cutter 20 or the tubular section 15.

While particular forms of the invention have been illustrated and described herein, it will be apparent that various modifications and improvements can be made to the invention. For example, while the various embodiments of the invention have been described herein in terms of a biopsy device, it should be apparent that the devices and methods of utilizing the device may be employed to remove tissue for purposes other than for biopsy, i.e. for treatment or other diagnoses. Other modifications include, for example, a tissue cutter slidably mounted around the tubular section of the probe component rather than within the tubular section. Moreover, individual features of embodiments of the invention may be shown in some drawings and not in others, but those skilled in the art will recognize that individual features of one embodiment of the invention can be combined with any or all the features of another embodiment. Accordingly, it is not intended that the invention be limited to the specific embodiments illustrated. It is therefore intended that this invention to be defined by the scope of the appended claims as broadly as the prior art will permit.

Terms such as "element", "member", "device", "section", "portion", "means", "step" and words of similar import, when used herein, shall not be construed as invoking the provisions of 35 U.S.C. § 112(6) unless the following claims expressly use the term "means" followed by a particular function without specific structure or the term "step" followed by a particular function without specific action. All patents and patent applications referred to above are hereby incorporated by reference in their entirety.

What is claimed is:

1. A method for collecting one or more tissue specimens from a target site within a patient, comprising:
   a. providing a biopsy device having:
      i. a disposable elongated probe component comprising:
         an elongated tubular section which has a longitudinal axis, which has an inner lumen extending therein, which has a penetrating distal tip and which has a tissue receiving aperture proximal to the penetrating distal tip configured to receive tissue from the target site,
         a first driven gear coupled to the elongated tubular section and configured to rotate, to in turn rotate the elongated tubular section around the longitudinal axis,
         an elongated tissue cutting member which is disposed within the elongated tubular section, which has a distal end having at least one tissue cutting edge and which has an inner lumen extending therein, the elongated tissue cutting member having a proximal end opposite the distal end, and
         a second driven gear coupled to the elongated tissue cutting member and configured to rotate to longitudinally move the elongated tissue cutting member relative to the elongated tubular section along the longitudinal axis,
         the first driven gear and the second driven gear being arranged coaxially and adjacent each other on the longitudinal axis;
      ii. a driver component configured to receive a proximal portion of the disposable elongated probe component in an operational relationship, the driver component having:
         a first driver unit configured to rotate the elongated tubular section of the disposable elongated probe component to orient the tissue receiving aperture of the elongated tubular section, the first driver unit having a first drive gear, and
         a second driver unit configured to drive the elongated tissue cutting member longitudinally within the elongated tubular section to cut a tissue specimen from the tissue received in the tissue receiving aperture of the elongated tubular section, the second driver unit having a second drive gear positioned adjacent the first drive gear, the first drive gear and the second drive gear of the driver component configured to respectively drivably engage the first driven gear and the second driven gear that are arranged coaxially and adjacent to each other on the longitudinal axis; and iii. a tissue collection device located at the proximal end of the elongated tissue cutting member, a portion of the elongated tissue cutting member being positioned inside the tissue collection device;

b. advancing the disposable elongated probe component at least partially into or adjacent to tissue at the target site;

c. rotating the elongated tubular section about the longitudinal axis by the first driver unit to a predetermined aperture orientation of the tissue receiving aperture;

d. applying a vacuum within the elongated tubular section to draw the tissue at the tissue site through the tissue receiving aperture of the elongated tubular section into an interior thereof;

e. advancing the elongated tissue cutting member longitudinally within the elongated tubular section by the second driver unit to cut the tissue specimen from the tissue extending into the elongated tubular section; and f. applying a vacuum to the proximal end of the elongated tissue cutting member for transporting the cut tissue specimen through the inner lumen of the elongated tissue cutting member to discharge the cut tissue specimen directly from the proximal end of the elongated tissue cutting member into the tissue collection device.

2. The method of claim 1, comprising:

providing the disposable elongated probe component with a third driven gear coupled to the elongated tissue cutting member, the third driven gear being arranged on the longitudinal axis such that the third driven gear is coaxial with the first driven gear and the second driven gear on the longitudinal axis;

providing the driver component with a third driver unit having a third drive gear configured to drivably engage the third driven gear, the third drive gear positioned adjacent the second drive gear; and driving the third driven gear with the third drive gear simultaneously with driving the second driven gear with the second drive gear, such that the act of advancing the elongated tissue cutting member longitudinally is achieved by driving the second driven gear and the act of advancing the elongated tissue cutting member longitudinally is accompanied by a rotational or oscillation motion of the elongated tissue cutting member about the longitudinal axis by driving the third driven gear.

3. The method of claim 1, comprising rotating the first driven gear in discrete rotational increments to in turn rotate the elongated tubular section about the longitudinal axis in discrete rotational increments.

4. The method of claim 3, wherein the discrete rotational increments are increments of 30 degrees.

5. The method of claim 3, wherein the discrete rotational increments are multiples of 30 degrees.

6. A method for collecting a tissue specimen from a target site within a patient, comprising:

a. providing a biopsy device having:

i. a disposable elongated probe component comprising:
an elongated tubular section which has a longitudinal axis, which has an inner lumen extending therein, which has a penetrating distal tip and which has a tissue receiving aperture proximal to the penetrating distal tip configured to receive tissue from the target site, a first driven gear coupled to the elongated tubular section, an elongated tissue cutting member which is disposed within the elongated tubular section, which has a distal end having at least one tissue cutting edge and which has an inner lumen extending therein, the elongated tissue cutting member having a proximal end opposite the distal end, a second driven gear coupled to the elongated tissue cutting member, and a third driven gear coupled to the elongated tissue cutting member, wherein the first driven gear, the second driven gear, and the third driven gear are coaxial with each other on the longitudinal axis;

ii. a driver component which is configured to receive a proximal portion of the elongated probe component in an operational relationship, which has:

a first driver unit configured to rotate the elongated tubular section of the elongated probe component to orient the tissue receiving aperture of the elongated tubular section, the first driver unit having a first drive gear configured to drivably engage the first driven gear of the elongated tubular section for rotating the elongated tubular section to position the tissue receiving aperture, a second driver unit configured to drive the elongated tissue cutting member longitudinally within the elongated tubular section to cut the tissue specimen from the tissue received in the tissue receiving aperture of the elongated tubular section, the second driver unit having a second drive gear positioned adjacent the first drive gear, the second drive gear configured to drivably engage the second driven gear for longitudinally moving the elongated tissue cutting member relative to the elongated tubular section, and a third driver unit configured to drive the elongated tissue cutting member in rotational or oscillation motion, the third driver unit having a third drive gear positioned adjacent the second drive gear, and configured to drivably engage the third driven gear for moving the elongated tissue cutting member in the rotational or oscillation motion; and iii. a tissue collection device located at the proximal end of the elongated tissue cutting member;

b. advancing the elongated probe component at least partially into the patient at the target site;

c. rotating the elongated tubular section about the longitudinal axis to a predetermined aperture orientation of the tissue receiving aperture by the first driver unit;

d. applying a first vacuum within the elongated tubular section to draw the tissue at the tissue site through the tissue receiving aperture of the elongated tubular section into an interior thereof;

e. advancing the elongated tissue cutting member longitudinally within the elongated tubular section by the second driver unit, and rotating or oscillating the elongated tissue cutting member within the elongated tubular section by the third driver unit, to cut the tissue specimen from the tissue drawn into the elongated tubular section; and f. applying a second vacuum to the proximal end of the elongated tissue cutting member for transporting the tissue specimen through the inner lumen of the elongated tissue cutting member to discharge the cut tissue specimen directly from the proximal end of the elongated tissue cutting member into the tissue collection device.

7. A method of operating a biopsy device, comprising:
a. providing a biopsy device having:
  i. a disposable elongated probe component including:
    an elongated tubular section which has a longitudinal axis, which has an inner lumen extending therein, which has a penetrating distal tip and which has a tissue receiving aperture proximal to the penetrating distal tip configured to receive tissue from a target site, and
    an elongated tissue cutting member which is disposed within the elongated tubular section, which has a distal end having at least one tissue cutting edge and which has an inner lumen extending therein, the elongated tissue cutting member having a proximal end opposite the distal end;
  ii. a driver component which is configured to receive a proximal portion of the elongated probe component in an operational relationship, which has:
    a first driver unit configured to rotate the elongated tubular section of the elongated probe component to orient the tissue receiving aperture of the elongated tubular section,
    a second driver unit configured to drive the elongated tissue cutting member longitudinally within the elongated tubular section to cut a tissue specimen from the tissue received in the tissue receiving aperture of the elongated tubular section,
    a third driver unit configured to drive the elongated tissue cutting member in rotational or oscillation motion; and
  iii. a first driven gear coupled to the elongated tubular section;
  iv. a second driven gear coupled to the elongated tissue cutting member;
  v. a third driven gear coupled to the elongated tissue cutting member, wherein the first driven gear, the second driven gear, and the third driven gear are coaxial with each other on the longitudinal axis;
  vi. the first driver unit having a first drive gear configured to drivably engage the first driven gear of the elongated tubular section for rotating the elongated tubular section to position the tissue receiving aperture;
  vii. the second driver unit having a second drive gear positioned adjacent the first drive gear, the second drive gear configured to drivably engage the second driven gear for longitudinally moving the elongated tissue cutting member relative to the elongated tubular section; and
  viii. the third driver unit having a third drive gear positioned adjacent the second drive gear, and configured to drivably engage the third driven gear for moving the elongated tissue cutting member in the rotational or oscillation motion;
b. rotating the elongated tubular section about the longitudinal axis to a predetermined aperture orientation of the tissue receiving aperture by the first driver unit;
c. advancing the elongated tissue cutting member longitudinally within the elongated tubular section by the second driver unit; and
d. rotating or oscillating the elongated tissue cutting member within the elongated tubular section by the third driver unit.

8. The method of claim 7, comprising driving the first driven gear in discrete rotational increments to in turn rotate the elongated tubular section about the longitudinal axis in discrete rotational increments.

9. The method of claim 8, wherein the discrete rotational increments are increments of 30 degrees.

10. The method of claim 8, wherein the discrete rotational increments are multiples of 30 degrees.

11. The method of claim 7, wherein a driving of the third driven gear is simultaneous with a driving of the second driven gear.

* * * * *